# United States Patent

Choy et al.

(10) Patent No.: US 8,633,321 B2
(45) Date of Patent: Jan. 21, 2014

(54) SYNTHESIS OF (4-FLUORO-3-PIPERIDIN-4-YL-BENZYL)-CARBAMIC ACID TERT-BUTYL ESTER AND INTERMEDIATES THEREOF

(75) Inventors: Nakyen Choy, Belle Mead, NJ (US); John J. Shay, Jr., Bethlehem, PA (US); Adam W. Sledeski, Belle Mead, NJ (US)

(73) Assignee: Sanofi-Aventis U.S. LLC, Bridgewater, NJ (US)

( * ) Notice: Subject to any disclaimer, the term of this patent is extended or adjusted under 35 U.S.C. 154(b) by 0 days.

(21) Appl. No.: 13/426,721

(22) Filed: Mar. 22, 2012

(65) Prior Publication Data

US 2012/0184745 A1  Jul. 19, 2012

Related U.S. Application Data

(63) Continuation of application No. PCT/US2010/049737, filed on Sep. 22, 2010.

(60) Provisional application No. 61/245,325, filed on Sep. 24, 2009.

(51) Int. Cl.
  *C07D 211/02* (2006.01)
(52) U.S. Cl.
  USPC ............................................... 546/185
(58) Field of Classification Search
  USPC ............................................... 546/185
  See application file for complete search history.

(56) References Cited

FOREIGN PATENT DOCUMENTS

| WO | WO 01/13811 A1 | 3/2001 |
| WO | WO 2005/097780 A1 | 10/2005 |
| WO | WO 2005-111003 | * 11/2005 |
| WO | WO 2011/037947 A1 | 3/2011 |

OTHER PUBLICATIONS

Barberis, et al., Rapid Access to N-Boc Phenylglycine Derivatives via Benzylic Lithiation Reactions, Tetrahedron, vol. 57, (2001). pp. 2965-2972.
Vaz, et al., Design of Bivalent Ligands Using Hydrogen Bond Linkers: Synthesis and Evaluation of Inhibitors for Human B-Tryptase, Bioorganic & Medicinal Chemistry Letters, vol. 14, (2004), pp. 6053-6056.
Franconi, et al., Mast Cell Tryptase and Chymase Reverse Airway Smooth Muscle Relaxation Induced by Vasoactive Intestinal Peptide in the Ferret, The Journal of Pharmacology and Experimental Therapeutics, (1989), vol. 248, No. 3, pp. 847-951.
Sekizawa, et al., Mast Cell Tryptase Causes Airway Smooth Muscle Hyperresponisiveness in Dogs, J. Clin. Invest., vol. 83, (1989), pp. 175-179.
Tam, et al., Degradation of Airway Neuropeptides by Human Lung Tryptase, Am J. Respir. Cell Mol. Biol vol. 3, (1990), pp. 27-32.
Caughey, et al., Substance P and Vasoactive Intestinal Peptide Degradation by Mast Cell Tryptase and Chymase, The Journal of Pharmacology and Experimental Therapeutics, (1998), vol. 244, No. 1, pp. 133-137.

* cited by examiner

*Primary Examiner* — John Mabry
(74) *Attorney, Agent, or Firm* — Ronald G. Ort

(57) ABSTRACT

The present invention is an improved method for the preparation of (4-fluoro-3-pyridin-4-yl-benzyl)-carbamic acid tert-butyl ester, compound of formula I. The invention is directed to a method of synthesis for the compound of formula I in three steps, comprising formation of 5-((tert-butoxycarbonyl)aminomethyl)-2-fluorobenzeneboronic acid (compound 11), reaction of compound 11 under Suzuki coupling conditions to yield (4-fluoro-2-pyridin-4-yl-benzyl)-carbamic acid tert-butyl ester and selective hydrogenation of the aforementioned product under hydrogenation conditions yields compound I. The invention is also directed to the intermediates 5-((tert-butoxycarbonyl)amino-methyl)-2-fluorobenzeneboronic acid (compound 11), and (4-fluoro-3-pyridin-4-yl-benzyl)-carbamic acid tert-butyl ester (compound 13).

31 Claims, No Drawings

SYNTHESIS OF (4-FLUORO-3-PIPERIDIN-4-YL-BENZYL)-CARBAMIC ACID TERT-BUTYL ESTER AND INTERMEDIATES THEREOF

FIELD OF THE INVENTION

This invention is directed to a method of synthesis of 4-fluoro-3-piperidin-4-yl-benzyl)-carbamic acid tert-butyl ester (I), and the intermediates thereof.

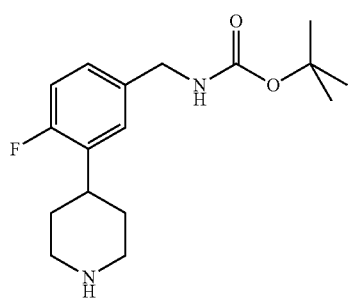

(I)

BACKGROUND OF THE INVENTION

WO2001/13811 discloses compounds including [(benzylamine)-piperidin-1-yl] (aryl or heteroaryl)methanone as tryptase inhibitors, and describes potential uses for such compounds due to tryptase being implicated in a variety of biological processes, including degradation of vasodilating and bronchorelaxing neuropeptides (Caughey, et al., J. Pharmacol. Exp. Ther., 1988, 244, pages 133-137; Franconi, et al., J. Pharmacol. Exp. Ther., 1988, 248, pages 947-951; and Tam, et al., Am. J. Respir. Cell Mol. Biol., 1990, 3, pages 27-32) and modulation of bronchial responsiveness to histamine (Sekizawa, et al., J. Clin. Invest., 1989, 83, pages 175-179).

WO2005/097780 more particularly discloses the (benzylamine)-piperidin-1-yl thienylmethanone compound of formula A, its preparation, and use for treating disease states

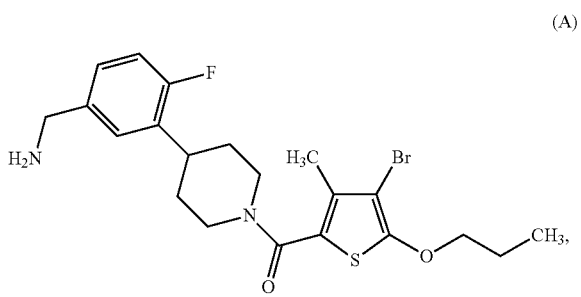 [SMILES: CCCOc1sc(C(=O)N2CCC(c3cc(CN)ccc3F)CC2)c(C)c1Br]

(A)

capable of being modulated by the inhibition of tryptase. WO2005/097780 also discloses that the compound of the formula A is prepared through the coupling of the following compounds 14 and I as shown in Scheme A, and subsequent deprotection of the coupled product.

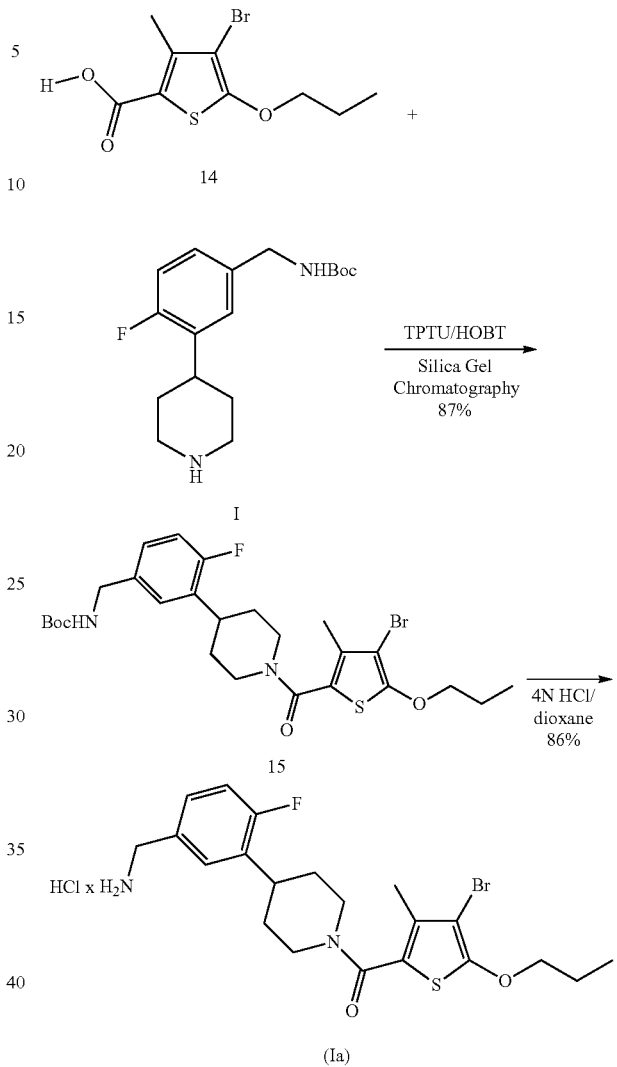

Compound I was prepared by the seven step synthesis as shown in the below Scheme B.

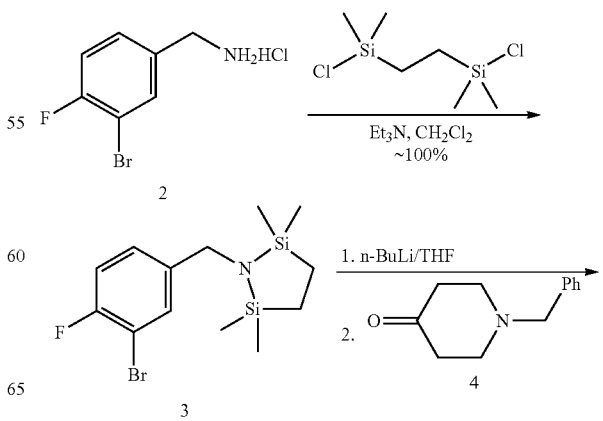

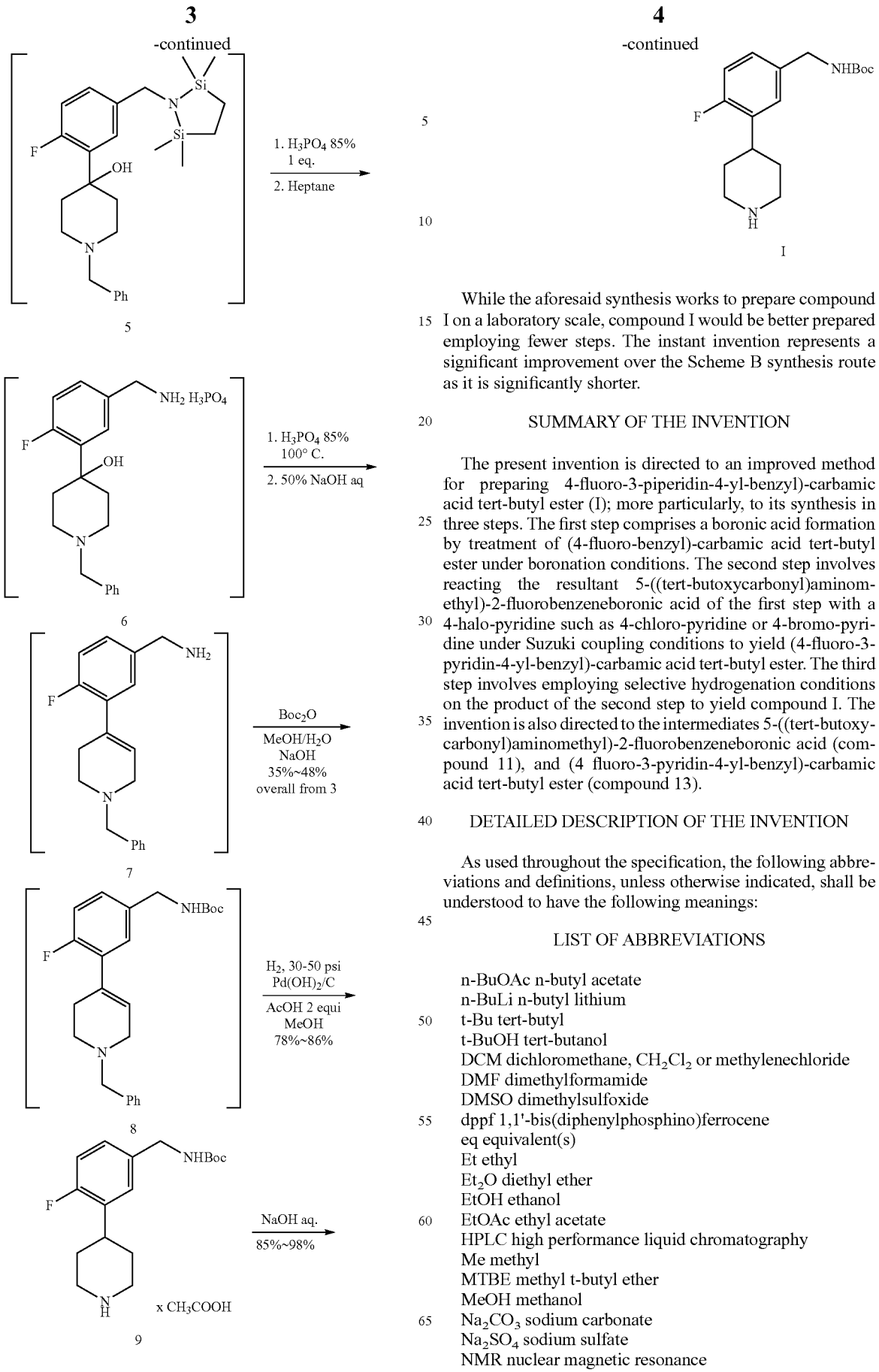

While the aforesaid synthesis works to prepare compound I on a laboratory scale, compound I would be better prepared employing fewer steps. The instant invention represents a significant improvement over the Scheme B synthesis route as it is significantly shorter.

SUMMARY OF THE INVENTION

The present invention is directed to an improved method for preparing 4-fluoro-3-piperidin-4-yl-benzyl)-carbamic acid tert-butyl ester (I); more particularly, to its synthesis in three steps. The first step comprises a boronic acid formation by treatment of (4-fluoro-benzyl)-carbamic acid tert-butyl ester under boronation conditions. The second step involves reacting the resultant 5-((tert-butoxycarbonyl)aminomethyl)-2-fluorobenzeneboronic acid of the first step with a 4-halo-pyridine such as 4-chloro-pyridine or 4-bromo-pyridine under Suzuki coupling conditions to yield (4-fluoro-3-pyridin-4-yl-benzyl)-carbamic acid tert-butyl ester. The third step involves employing selective hydrogenation conditions on the product of the second step to yield compound I. The invention is also directed to the intermediates 5-((tert-butoxycarbonyl)aminomethyl)-2-fluorobenzeneboronic acid (compound 11), and (4 fluoro-3-pyridin-4-yl-benzyl)-carbamic acid tert-butyl ester (compound 13).

DETAILED DESCRIPTION OF THE INVENTION

As used throughout the specification, the following abbreviations and definitions, unless otherwise indicated, shall be understood to have the following meanings:

LIST OF ABBREVIATIONS n-BuOAc n-butyl acetate
n-BuLi n-butyl lithium
t-Bu tert-butyl
t-BuOH tert-butanol
DCM dichloromethane, $CH_2Cl_2$ or methylenechloride
DMF dimethylformamide
DMSO dimethylsulfoxide
dppf 1,1'-bis(diphenylphosphino)ferrocene
eq equivalent(s)
Et ethyl
$Et_2O$ diethyl ether
EtOH ethanol
EtOAc ethyl acetate
HPLC high performance liquid chromatography
Me methyl
MTBE methyl t-butyl ether
MeOH methanol
$Na_2CO_3$ sodium carbonate
$Na_2SO_4$ sodium sulfate
NMR nuclear magnetic resonance Pd(PPh$_3$)$_4$ tetrakistriphenylphosphine palladium
Pd(PPh$_3$)$_2$Cl$_2$ bistriphenylphosphine palladium (II) dichloride
PdCl$_2$dppf 1,1'-bis(diphenylphosphino) ferrocene palladium (II) dichloride
Pd(dtbpf)Cl$_2$ (1,1'Bis(di-t-butylphosphino)ferrocene palladium dichloride
Pd$_2$(dba)$_3$ tris(dibenzylideneacetone)dipalladium(0)
Pd(OAc)$_2$ palladium(II) acetate
P(Cy)$_3$ tricyclohexylphosphine
t-Bu$_3$P tri-t-butylphosphine
PPh$_3$ triphenylphosphine
PrOH propanol
i-PrOH iso-propanol
i-PrOAc iso-propyl acetate
t-BuOK potassium tert-butoxide
PPSE poly-phosphoric acid trimethylsilylester
rt room temperature
Rt Retention time
TFA trifluoroacetic acid
TFAA trifluoroacetic anhydride
THF tetrahydrofuran
TLC thin layer chromatography

TERMS

"aqueous acid" means an aqueous solution of an inorganic (mineral) acid such as hydrochloric acid, phosphoric acid and the like, or an aqueous solution of an organic acid such as acetic acid and the like.

"boronation conditions" mean conditions using a superbase, a boronic acid forming agent, boronation solvent, and boronation reaction temperature.

"superbase" means an extremely strong base, such as combination of an organolithium reagent of formula RLi where R is an alkyl or aryl group having 1-12 carbons and a bulky potassium alkoxide such as potassium tert-butoxide or potassium tert-pentoxide and the like.

"boronic acid forming agent" means a trialkyl boronate such as trimethyl borate, triethyl borate, tripropyl borate, triisopropyl borate, tributylborate and the like.

"boronation solvent" means a solvent an ether solvent such as diethyl ether, THF, 2-methyltetrahydrofuran, MTBE, dimethoxyethane and the like "boronation temperature" means from about −30 to −100° C.

"4-halopyridine" means 4-(iodo, bromo or chloro)pyridine, or salt thereof

"Suzuki coupling conditions" mean conditions using a Suzuki coupling solvent, Suzuki coupling catalyst and Suzuki coupling reaction temperature.

"Suzuki coupling solvent" means an alcohol solvent with a boiling point of isopropyl alcohol, such as n-propyl alcohol, n-butyl alcohol or the like; polar aprotic solvent such as dimethylformamide, 1-methyl-2-pyrrolidone, dimethylsulfoxide, or the like; ether solvent such as THF, 2-methylTHF, dimethoxyethane, MTBE or the like; or mixture of any of the aforesaid mentioned solvents and water or toluene.

"Suzuki coupling catalyst" means a Pd catalyst such as Pd(PPh$_3$)$_4$, Pd(PPh$_3$)$_2$Cl$_2$, Pd$_2$(dba)$_3$, PdCl$_2$dppf, Pd(dtbpf)Cl$_2$, or the like; or Pd catalyst such as Pd(OAc)$_2$, Pd$_2$(dba)$_3$ or the like in conjunction with a phosphine ligand such as PPh$_3$, dppf, t-Bu$_3$P, P(Cy)$_3$ or the like.

"Suzuki coupling reaction temperature" means a temperature from about 60° C. to about 100° C., the temperature of the boiling point of the Suzuki coupling reaction mixture.

"hydrogenation conditions" means conditions using a hydrogenation catalyst, hydrogenation solvent, hydrogenation reaction temperature, and hydrogenation pressure.

"hydrogenation reaction solvent" means an ester solvent such as EtOAc, i-PrOAc, BuOAc and the like; alcohol solvent such as methanol, ethanol, isopropyl alcohol and the like; or AcOH; or a mixture of an alcohol or ester solvent and water and acetic acid "hydrogenation catalyst" means Pt/C, PtO$_2$, Pd/C, Pd(OH)$_2$, Rh/C and the like, with or without added inorganic acid such as HCl and the like, or organic acid such as acetic acid and the like.

"hydrogenation reaction temperature" means from about 10 to about 60° C.

"hydrogenation pressure" means from about 10 to about 1000 psi of hydrogen (upper limit dictated by equipment capability).

Particular Embodiments

In a particular embodiment of the method according to the present invention, the superbase means combination of n-butyl lithium and potassium tert-butoxide ("Schlosser base").

In another particular embodiment of the method according to the present invention, "boronation solvent" means THF.

In another particular embodiment of the method according to the present invention, "boronic acid forming agent" means triisopropyl borate.

In another particular embodiment of the method according to the present invention, the boronation temperature is about −70° C. to about −45° C.

In another particular embodiment of the method according to the present invention, the Suzuki coupling solvent is dimethoxyethane.

In another particular embodiment of the method according to the present invention, the Suzuki coupling catalyst is Pd(PPh$_3$)$_4$.

In another particular embodiment of the method according to the present invention, the Suzuki coupling is effected at about 85° C.

In another particular embodiment of the method according to the present invention, the hydrogenation solvent is EtOAc.

In another particular embodiment of the method according to the present invention, the hydrogenation catalyst is Pt/C.

In another particular embodiment of the method according to the present invention, the hydrogenation reaction temperature is at about ambient temperature.

In another particular embodiment of the method according to the present invention, the hydrogenation pressure is from about 10 to about 60 psi.

Preparatory Details

The starting materials for preparing compound I according to Scheme 1 below are commercially available.

Scheme 1

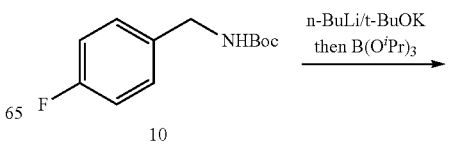

10

-continued

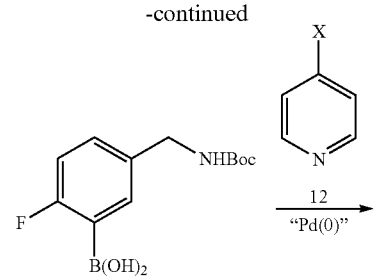

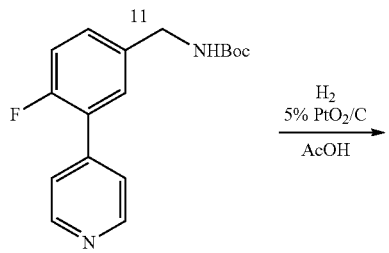

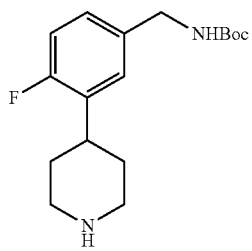

4-(tert-Butoxycarbonyl)aminomethyl)-fluorobenzene (compound 10), prepared according to the method of Tetrahedron 2965, 57, 2001 which is incorporated herein by reference, is reacted with a superbase, in an ether solvent at a sufficiently low temperature as for example from about −100° C. to about −30° C. The resultant mixture is reacted with boronic acid forming agent. Quenching the resultant mixture with an aqueous acid provides 5-((tert-butoxycarbonyl)aminomethyl)-2-fluorobenzeneboronic acid (compound 11). Compound 11 is reacted with a 4-halopyridine (compound 12) or their hydrohalide salt forms in an alcoholic solvent with a boiling point of at least that of isopropyl alcohol, a polar aprotic solvent or an ether solvent. Compound 11 and compound 12 in mixture of any of the above mentioned solvents and water in the presence of a suitable Suzuki coupling catalyst at Suzuki coupling reaction temperature provides compound 13.

Compound 13 is reduced under hydrogenation conditions to compound I by treatment with hydrogen in the presence of a hydrogenation catalyst, with or without added inorganic acid such as HCl and the like, or organic acid such as acetic acid and the like, in a hydrogenation reaction solvent; at hydrogenation reaction temperature, and hydrogenation pressure.

EXAMPLE

The present invention may be better understood by reference to the following non-limiting Example, which is exemplary of the invention. The following example is presented in order to more fully illustrate a particular embodiment of the invention. They should in no way be construed, however, as limiting the broad scope of the invention.

In the nuclear magnetic resonance spectra (NMR), reported infra, the chemical shifts are expressed in ppm relative to tetramethylsilane. Abbreviations have the following significances: br=broad, dd=double doublet, s=singlet; m=multiplet.

Example 1

Step A: Preparation of 5-((tert-Butoxycarbonyl)aminomethyl)-2-fluorobenzeneboronic acid (11)

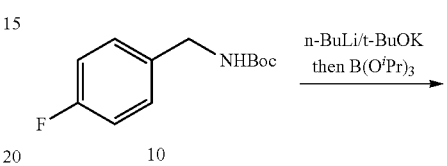

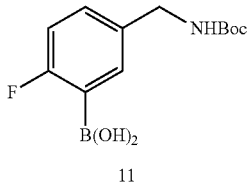

To a mixture of 4-(tert-Butoxycarbonyl)aminomethyl)-fluorobenzene (*Tetrahedron* 2001, 57, page 2965 which is incorporated herein by reference) (2.84 g 12.6 mmol) and t-BuOK (2.83 g, 12.6 mmol) in THF (40 mL) at −60 to −70° C., is added n-BuLi (15.75 mL, 1.6 M, 25.2 mmol) over a period of approximately 10 min. The reaction mixture is stirred at this temperature for additional 1.5 h, after which triisopropyl borate (2.37 g, 12.6 mmol) is added. The mixture is allowed to warm to −45° C., after which it was quenched with 2N aqueous HCl. The reaction mixture is allowed to warm to room temperature with stirring overnight. The resulting suspension is isolated by filtration and dried in a vacuum oven to afford 1.9 g (56%) of compound 11 as a white solid. $^1$H NMR (300 MHz, CDCl$_3$) δ 7.72 (m, 1H), 7.38 (m, 1H), 7.01 (m, 1H), 5.22 (d, J=6.1 Hz, 2H), 4.28 (d, J=5.4 Hz, 2H), 1.45 (s, 9H).

Step B: Preparation of (4-fluoro-3-pyridin-4-yl-benzyl)-carbamic acid tert-butyl ester (13)

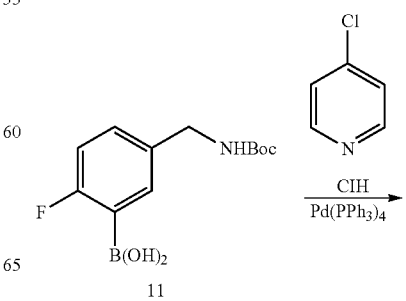

-continued

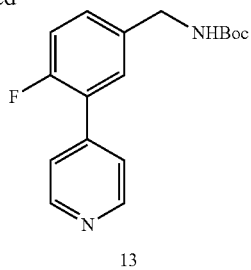

13

A mixture of compound 11 (135 mg, 0.5 mmol), 4-chloropyridine hydrochloride (107 mg, 0.713 mmol), tetrakis(triphenylphosphine)palladium (45 mg, 0.04 mmol) and $Na_2CO_3$ (160 mg, 1.51 mmol) in dimethoxyethane (2.2 mL) and water (0.7 mL) mixture, is heated to 85° C. for 5 h. The mixture is cooled to rt and partitioned between water and EtOAc. The organic phase is dried using $Na_2SO_4$ and concentrated on rotary evaporator to afford 100 mg (59%) of compound 13. $^1$H NMR (300 MHz, $CDCl_3$) δ 8.68-8.62 (m, 2H), 7.80-7.42 (m, 2H), 7.40-7.35 (m, 1H), 7.36-7.24 (m, 1H), 7.18-7.08 (m, 1H), 5.26-5.18 (br s, 1H), 4.25 (d, J=5.5 Hz, 2H), 1.44 (s, 9H).

Step C: Preparation of (4-Fluoro-3-piperidin-4-yl-benzyl)-carbamic acid tert-butyl ester hydrochloride (I)

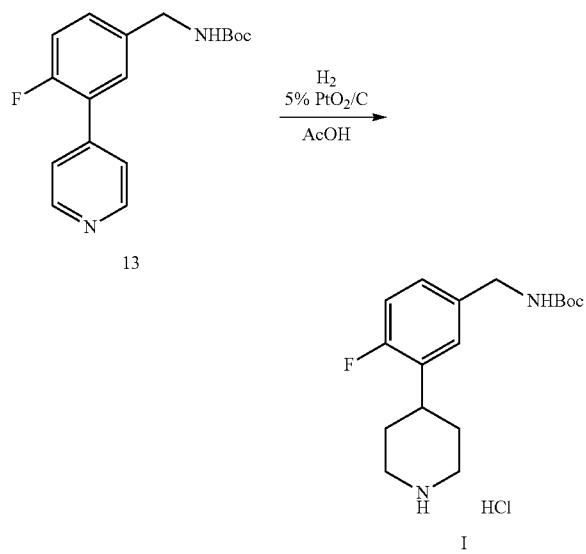

A mixture of compound 13 (1.25 g, 4.1 mmol) and $PtO_2$ (200 mg) in EtOAc (20 mL) and acetic acid (10 mL) is hydrogenated in a Parr shaker under $H_2$ (50 psi-60 psi) overnight. n-BuOAc is added (40 mL) to the mixture. The resultant suspension is filtered through Celite, and concentrated up to around 30 mL of crude solution. The crude solution was introduced to a solution of 2N HCl in ethyl ether (5 mL) and MTBE (35 mL) at 0° C. The resultant solid is collected by filtration followed by washing with an additional MTBE and drying in oven at 50° C. to give 0.93 (65%) g of product I as an HCl salt.
$^1$H NMR (300 MHz, DMSO-d6) δ 9.30-9.10 (br s, 2H), 7.44-7.35 (m, 1H), 7.16-7.03 (m, 3H), 4.08 (d, J=6.0 Hz, 2H), 3.31 (br s, 2H), 3.20-2.87 (m, 3H), 1.95-1.80 (m, 4H), 1.39 (s, 9H).

What is claimed is:

1. A method for preparing 5-((tert-butoxycarbonyl)aminomethyl)-2-fluorobenzene-boronic acid, comprising boronation of 4-(tert-butoxycarbonyl)aminomethyl)-fluorobenzene with a boronic acid forming agent under boronation conditions, and then quenching the resultant mixture with an aqueous acid to yield 5-((tert-butoxycarbonyl)aminomethyl)-2-fluoro-benzeneboronic acid.

2. The method of claim 1 wherein the boronation conditions uses a superbase.

3. The method of claim 2 wherein the superbase is a combination of an organolithium reagent of formula RLi where R is an alkyl or aryl group having 1-12 carbons and a bulky potassium alkoxide such as potassium tert-butoxide or potassium tert-pentoxide and the like.

4. The method of claim 3 wherein the superbase is a combination of n-butyllithium and potassium tert-butoxide.

5. The method of claim 1 wherein the boronation conditions uses a boronic acid forming agent which is a trialkyl boronate.

6. The method of claim 5 wherein the trialkyl boronate is selected from trimethyl borate, triethyl borate, tripropyl borate, triisopropyl borate, tributylborate and the like.

7. The method of claim 6 wherein the trialkyl boronate is triisopropyl borate.

8. The method of claim 1 wherein the boronation conditions uses a boronation solvent which is an ether solvent selected from diethyl ether, THF, 2-methyltetrahydrofuran, MTBE, dimethoxyethane and the like.

9. The method of claim 8 wherein the ether solvent is THF.

10. The method of claim 1 wherein the boronation conditions uses a boronation reaction temperature from about −100° C. to about −30° C.

11. The method of claim 10 wherein the boronation reaction temperature is from about −70° C. to about −45° C.

12. The method of claim 1 wherein the aqueous acid is HCl or $H_3PO_4$.

13. The method of claim 12 wherein the aqueous acid is HCl.

14. A method for preparing (4-fluoro-3-pyridin-4-yl-benzyl)-carbamic acid tert-butyl ester comprising coupling 5-((tert-butoxycarbonyl)aminomethyl)-2-fluorobenzeneboronic acid prepared according to claim 1 and a 4-halopyridine under Suzuki coupling conditions to yield 4-fluoro-3-pyridin-4-yl-benzyl)-carbamic acid tert-butyl ester.

15. The method according to claim 14 wherein the Suzuki coupling conditions uses a Suzuki coupling solvent selected from an alcoholic solvent with a boiling point of at least that of i-propyl alcohol, polar aprotic solvent, or ether solvent, or mixture of any of the aforesaid mentioned solvents and water or toluene.

16. The method according to claim 15 wherein the Suzuki coupling solvent is an ether solvent selected from THF, toluene, 2-methylTHF, or dimethoxyethane.

17. The method according to claim 16 wherein the ether solvent is dimethoxyethane.

18. The method according to claim 14 wherein the Suzuki coupling conditions uses a Suzuki catalyst selected from Pd catalyst such as $Pd(PPh_3)_4$, $Pd(PPh_3)_2Cl_2$, $Pd_2(dba)_3$, $PdCl_2dppf$, $Pd(dtbpf)Cl_2$, or the like; or Pd catalyst such as $Pd(OAc)_2$, $Pd_2(dba)_3$ or the like in conjunction with a phosphine ligand such as $PPh_3$, dppf, $t-Bu_3P$, $P(Cy)_3$ or the like, and a strong base.

19. The method according to claim 18 wherein the Suzuki coupling catalyst is Pd(PPh$_3$)$_4$.

20. The method according to claim 14 wherein the Suzuki coupling conditions uses a Suzuki coupling reaction temperature of from about 60° C. to about 100° C.

21. The method according to claim 20 wherein the Suzuki coupling reaction temperature is at about 85° C.

22. The method in claim 14 wherein the 4-halopyridine is 4-chloropyridine.

23. A method for preparing (4-fluoro-3-piperidin-4-yl-benzyl)-carbamic acid tert-butyl ester hydrochloride (I), comprising reducing (4-fluoro-3-pyridin-4-yl-benzyl)-carbamic acid tert-butyl ester prepared according to claim 14 under hydrogenation reducing conditions, and then followed by HCl work-up to yield fluoro-3-piperidin-4-yl-benzyl)-carbamic acid tert-butyl ester hydrochloride.

24. The method according to claim 23 wherein the hydrogenation reducing conditions uses a hydrogenation catalyst selected from Pt/C, PtO$_2$, Pd/C, Pd(OH)$_2$, Rh/C and the like, with or without added inorganic acid such as HCl and the like, or organic acid such as acetic acid and the like.

25. The method according to claim 24 wherein the hydrogenation catalyst is PtO$_2$.

26. The method according to claim 23 wherein the hydrogenation reducing conditions uses a hydrogenation solvent selected from an ester solvent such as EtOAc, i-PrOAc, BuOAc and the like; alcohol solvent such as methanol, ethanol, isopropyl alcohol and the like; or AcOH; or a mixture of an alcohol or ester solvent and water and acetic acid.

27. The method according to claim 26 wherein the hydrogenation solvent i-PrOAc.

28. The method according to claim 23 wherein the hydrogenation reducing conditions uses a hydrogenation reaction temperature from about 10 to about 60° C.

29. The method according to claim 23 wherein the hydrogenation reaction temperature is at about ambient temperature.

30. The method according to claim 23 wherein the hydrogenation reducing conditions uses a hydrogenation pressure from about 10 to about 1000 psi.

31. The method according to claim 30 wherein the hydrogenation pressure is from about 50 to about 60 psi.

* * * * *